United States Patent
Thorp et al.

(10) Patent No.: US 6,180,346 B1
(45) Date of Patent: Jan. 30, 2001

(54) ELECTROPOLYMERIZABLE FILM, AND METHOD OF MAKING AND USE THEREOF

(75) Inventors: H. Holden Thorp, Chapel Hill, NC (US); Allyn C. Ontko, Iowa City, IA (US)

(73) Assignee: The Universtiy of North Carolina at Chapel Hill, Chapel Hill, NC (US)

(*) Notice: Under 35 U.S.C. 154(b), the term of this patent shall be extended for 0 days.

(21) Appl. No.: 09/267,552

(22) Filed: Mar. 12, 1999

Related U.S. Application Data

(63) Continuation-in-part of application No. 08/667,338, filed on Jun. 20, 1996, now Pat. No. 5,871,918, which is a continuation-in-part of application No. 08/495,817, filed on Jun. 27, 1995, now abandoned, and a continuation-in-part of application No. 08/950,503, filed on Oct. 14, 1997, which is a continuation-in-part of application No. 08/667,337, filed on Jun. 20, 1996.

(51) Int. Cl.[7] .............. C12Q 1/68; C12M 1/34; C12C 1/15; G01N 27/26
(52) U.S. Cl. .............. 435/6; 435/288; 435/291; 435/810; 435/817; 204/153.12; 204/403; 204/412
(58) Field of Search .............. 204/153.12, 403; 204/412; 435/288, 291, 810, 817, 6

(56) References Cited

U.S. PATENT DOCUMENTS

| | | | |
|---|---|---|---|
| 4,545,382 | 10/1985 | Higgins et al. | 128/635 |
| 4,683,195 | 7/1987 | Mullis et al. | 435/6 |

(List continued on next page.)

FOREIGN PATENT DOCUMENTS

| | | | |
|---|---|---|---|
| 0 478 319 A1 | 4/1992 | (EP) | C12Q/1/68 |
| 572907 | * 12/1993 | (EP) | 435/6 |
| 3076600 | 4/1991 | (JP) | |
| WO 85/02627 | 6/1985 | (WO) | |
| WO 91/15768 | 10/1991 | (WO) | |
| 0478319A1 | * 1/1992 | (WO) | 204/153.12 |
| WO 93/20230 | 10/1993 | (WO) | |
| WO 94/22889 | 10/1994 | (WO) | |
| WO 95/00530 | 1/1995 | (WO) | |
| WO 97/02359 | 1/1997 | (WO) | |

OTHER PUBLICATIONS

Scneider et al., "Quantitative Aspects of ion exchange partition of redox cations into organosilane–styrene-sulfonate copolymer films on electrodes", Analytical Chemistry, vol. 54 (9), pp. 1508–1515, Aug. 1982.*

Livache et al.; Biosensing Effects in Flunctionalized Electroconducting Conjugated Polymer Layers: Addressable DNA Matrix for the Detection of Gene Mutations, Synthetic Metals, 71:pp. 2143–2146 (1995).

(List continued on next page.)

*Primary Examiner*—Jeffrey Fredman
*Assistant Examiner*—Arun Chakrabarti
(74) *Attorney, Agent, or Firm*—Myers Bigel Sibley & Sajovec

(57) ABSTRACT

An electrode and method of preparing an electrode by electropolymerizing a film on the conductive working surface of an electrode. The electrode is modified by reductive electropolymerization of a thin film of poly[Ru(vbpy)$_3^{2+}$] or poly[Ru(vbpy)$_3^{2+}$/vba] (vbpy=4-vinyl-4'methyl-2,2'-bipyridine and vba=p-vinylbenzoic acid) and the electrode is used for the electrochemical detection of aqueous GMP, poly[G], and surface immobilized single-stranded DNA probes. The film is formed from a co-polymer of a mediator such as Ru(vbpy)$_3^{2+}$ and a functionalized moiety having a carboxylate group such as p-vinylbenzoic acid. A DNA probe is attached covalently to the carboxylate group via a carbodiimide reaction followed by amidation of an amino-linked single-stranded DNA. In the presence of these guanine containing moieties, a dramatic enhancement in the oxidative current for the Ru$^{3+/2+}$ couple (present in the polymeric thin film) due to the catalytic oxidation of guanine is observed.

4 Claims, 8 Drawing Sheets

U.S. PATENT DOCUMENTS

| | | | |
|---|---|---|---|
| 4,704,353 | | 11/1987 | Humphries et al. ..................... 435/4 |
| 4,756,807 | * | 7/1988 | Meyer et al. ........................... 204/59 |
| 4,800,159 | | 1/1989 | Mullis et al. ..................... 435/172.3 |
| 4,840,893 | | 6/1989 | Hill et al. ................................. 435/6 |
| 4,883,579 | | 11/1989 | Humphries et al. ................. 204/403 |
| 4,908,307 | | 3/1990 | Rodland et al. ......................... 435/6 |
| 4,945,045 | | 7/1990 | Forrest et al. ......................... 435/25 |
| 4,963,815 | | 10/1990 | Hafeman ............................. 324/715 |
| 4,965,188 | | 10/1990 | Mullis et al. ............................ 435/6 |
| 5,066,372 | | 11/1991 | Weetall ............................ 204/153.1 |
| 5,108,889 | | 4/1992 | Smith ...................................... 435/4 |
| 5,112,974 | | 5/1992 | Barton ..................................... 546/4 |
| 5,143,854 | | 9/1992 | Pirrung et al. ........................ 436/518 |
| 5,157,032 | | 10/1992 | Barton ................................. 514/185 |
| 5,171,853 | | 12/1992 | Thorp et al. ........................... 536/27 |
| 5,175,082 | | 12/1992 | Jeffreys .................................... 435/6 |
| 5,194,372 | | 3/1993 | Nagai et al. ............................. 435/6 |
| 5,272,056 | | 12/1993 | Burrows ................................... 435/6 |
| 5,278,043 | | 1/1994 | Bannwarth et al. ................ 536/23.1 |
| 5,312,527 | * | 5/1994 | Mikkelsen et al. ............. 204/153.12 |
| 5,378,628 | | 1/1995 | Gratzel et al. ........................ 435/288 |
| 5,405,783 | | 4/1995 | Pirrung et al. ........................ 436/518 |
| 5,439,829 | | 8/1995 | Anderson et al. .................... 436/518 |
| 5,532,129 | | 7/1996 | Heller ....................................... 435/6 |
| 5,540,828 | | 7/1996 | Yacynych ............................. 204/418 |
| 5,565,322 | | 10/1996 | Heller ....................................... 435/6 |
| 5,605,662 | | 2/1997 | Heller et al. ......................... 422/68.1 |
| 5,632,957 | | 5/1997 | Heller et al. ......................... 422/68.1 |
| B1 4,683,202 | | 11/1990 | Mullis .................................... 435/91 |

OTHER PUBLICATIONS

Livache et al.; Preparation of a DNA Matrix Via An Electrochemically Directed Copolymerization of Pyrrole and Oligonucleotides Bearing a Pyrrole Group, *Nucleic Acids Research*, 22(15):pp. 2915–2921 (1994).

Roget et al.; Electrochemically Directed Copolymerization of Pyrrole and Oligonucleotides, *Nucleosides & Nucleotides*, 14(3–5):pp. 943–946 (1995).

H. Korri–Youssoufi et al.; Toward Bioelectronics: Specific DNA Recognition Based on an Oligonucleotide–Functionalized Polypyrrole, *American Chemical Society*, 2pp. (1997).

The Chip of the 90's, *Chemistry in Britain*, pp. 122–125 (Feb. 1995).

Carter et al.; Voltammetric Studies of the Interaction of Metal Chelates with DNA. 2. Tris–Chelated Complexes of Cobalt(III) and Iron(II) with 1.10–Phenanthroline and 2,2–Bipyridine, *J. Am. Chem. Soc.*, 111(24):pp. 8901–8911 (1989).

Chee et al.; Accessing Genetic Information High–Density DNA Arrays, *Science*, 274:pp. 610–614 (1996).

Daube et al.; Typing of *Clostridium perfringens*byIn Vitro Amplification of Toxin Genes, *Journal of Applied Bacteriology*, 77:pp. 650–655 (1994).

Du et al.; (10) Automated Fluorescent DNA Sequencing of Polymerase Chain Reaction Products, *Methods in Enzymology*, 218(104–121 (1993).

Fedorova et al.; Application of Tris(2,2–Bipyridyl)Ruthenium(III) for the Investigatioin of dNA Spatial Structure by a Chemical Modification Method, *J. of Inorganic Biochemistry*, 34: pp. 149–155 (1988).

Fodor et al., Multiplexed BiochemicalAssays with Biological Chips, *Product Review*, 364:pp. 555–565 (Aug. 5 1993).

Fodor et al.; Light–Directed, Spatially Addressable Parallel Chemical Synthesis, *Research Article*, pp. 767–773 (Feb. 15 1991).

Guatelli et al.; Isothermal in vitro Amplification of Nucleic Acids by a Multienzyme Reaction Modeled After Retroviral Replication, *Proc. Natl. Acad. Sci.*, 87:pp. 1874–1878 (1990).

Hall et al.; An Electrochemical Method for Detection of Nucleic Acid Hybridisation, *Biochemistry and Molecular Biology International*, 32(1): pp. 21–28 (1994).

Holodniy et al.; Determination of Human Immunodeficiency Virus RNA in Plasma and Cellular Viral DNA Genotype Zidovudine Resistance and VIRAL Load During Aidovudine–Didanosine Combination Therapy, *J. of Virolagy*, 69(6): pp. 3510–3516 (1995).

Jenkins et al.; A Sequence–Specific Molecular Light Switch: Tethering of an Oligonucleotide to a Dipyridophenazine Complex of Ruthenium(II), *J. Am. Chem. Soc.*, 114: pp. 8736–8738 (1992).

Johnston, et al.; Trans–Dioxorhenium(V)–Mediated Electrocatalytic Oxidation of DNA at Indium Tin–Oxide Electrodes: Voltammetric Detection of DNA Cleavage in Solution, *Inorg. Chem.*, 33(26): pp. 6388–6390 (1994).

Johnston et al.; Electrochemical Measurement of the Solvent Accessibility of Nucleobases Using Electron Transfer between DNA and Metal Complexes, *J. Am. Chem. Soc.*, 117(35): pp. 8933–3938 (1995).

Kwoh et al.; Target Amplification Systems in Nucleic Acid––Based Diagnostic Approaches, pp. 14–25, Oct. 1990.

Kwoh et al.; Transcription–Based Amplification System and Detection of Amplified Human Immunodeficiency Virus Type I with a Bead–Based Sandwich Hybridization Format, *Proc. Natl. Acad. Sci.*, 86: pp. 1173–1177 (1989).

Lewis, PCR's Competitors Are Alive and Well and Moving Rapidly Towards Commercialization, *Genetic Engineering News*, 3 pages (1992).

Lishanski et al.; Mutation Detection by Mismatch Binding Protein, MutS, in Amplified DNA: Application to the Cystic Fibrosis Gene, *Proc. Natl. Acad. Sci.*, 91: pp. 2674–2678 (1994).

Lizardi et al.; Exponential Amplification of Recombinant––RNA Hybridization Probes, *Bio/Technology*, 6: pp. 1197–1202 (1998).

Lulitanond et al; Detection of Herpes Simplex Virus Type 2 Bgl II N Fragment in Paraffin–Embedded Cervical Tissue Sections Using Nested Polymerase Chain Reaction, *Molecular and Cellular Probes*, 8: pp. 441–447 (1994).

Maeder et al.; Nonlinear Least–Squares Fitting of Multivariate Absorption Data, *Anal. Chem*, 62(20): pp. 2220–2224 (1994).

Maher III; Inhibition of T7 RNA Polymerase Initiation by Triple–Helical DNA Complexes: A Model for Artificial Gene Repression, *Biochemistry*, 31(33): pp. 7587–7594 (1992).

Marchand–Brynaert et al.; Surface Functionalization of Poly(ethylene terephthalate) Film and Membrane by Controlled Wet Chemistry: Chemical Characterization of Carboxylated Surfaces, *J. of Colloid and Interface Science*, 173: pp. 236–244 (1995).

W. John Martin; 33 Infectious Diseases, *The Polymerase Chain Reaction (K.B. Mullis, F. Ferre, R. A. Gibbs, Editors, ©1994 Birkhauser Boston*, pp. 406–417.

Meade et al.; Electron Transfer through DNA: Site–Specific Modification of Duplex DNA with Ruthenium Donors and Acceptors, *Angew. Chem. Int. Ed. Engl.*, 34(3): pp. 352–354 (1995).

Millan et al; Sequence–Selective Biosensor for DNA Based on Electroactive Hybridization Indicators, *Anal. Chem.*, 65(17): pp. 2317–2323 (1993).

Millan et al.; Voltammetric DNA Biosensor for Cystic Fibrosis Based on Modified Carbon Paste Electrode, *Anal. Chem.*, 66(18): pp. 2943–2948 (1994).

Murphy et al.; Long–Range Photoinduced Electron Transfer Through a DNA Helix, *Science*, 262: pp. 1025–1029 (1993).

Murphy et al.; Fast Photoinduced Electron Transfer Through DNA Intercalation, *Proc. Natl. Acad. Sci.*, 91: pp. 5315–5319 (1994).

Neubauer et al.; Prognostic Importance of Mutations in the Ras Proto–Oncogenes in De Novo Acute Myeloid Leukemia, *Blood*, 83(6): pp. 1603–1611 (1994).

Nielsen et al.; Sequence Selective Recognition of DNA by Strand Displacement with a Thymine–Substituted Polyamide, *Science*, 254: pp. 1497–1500 (1991).

DNA Sequencing on Chip, Compact Arrays of Probes May be Used for Ultrafast DNA Sequencing if Fabrication and Interpretation Problems Can Be Solved, *Analytical Chemistry*, 67(5): pp. 201 A–204A (1995).

Osteryoung; Voltammetry for the Future, *Acc. Chem. Res.*, 26(3): pp. 77–83 (1993).

Pyle et al.; Mixed–Ligand Complexes of Ruthenium(II): Factors Governing Binding to DNA, *J. Am. Chem. Soc.*, 111(8): pp. 3051–3058 (1989).

Ried et al.; Simultaneous Visualization of Seven Different DNA Probes by in situ Hybridization Using Combinatorial Fluorescence and Digital Imaging Microscopy, *Proc. Natl. Acad. Sci.*, 89: pp. 1388–1392 (1992).

Rudolph et al.; A Simulator for Cyclic Voltammetric Responses, *Analytical Chemistry*, 66(10):589 pp. A–600–A (1994).

Saleeba et al.; (19) Chemical Cleavage of Mismatch to Detect Mutatins, *Methods in Enzymology*, 217: pp. 286–295 (1993).

Satyanarayana et al.; Neither $\Lambda$l–nor $\Lambda$–Tris(Phenanthroline(Ruthenium(II) Binds to DNA by Classical Intercalation, *Biochemistry*, 31(39): pp. 9319–9324 (1992).

Schena et al.; Quantitative Monitoring of Gene Express Patterns with a Complementary DNA Microarray, *Science*, 270: pp. 467–470 (1995).

Mellors et al.; Prognosis in HIV–1 Infection Predicted by the Quantity of Virus in Plasma *Science*, 272: pp. 1167–1170 (1996).

Spargo et al.; Chemiluminescent Detection of Strand Displacement Amplified DNA from Species Comprising the *Mycobacterium tuberculosis*complex, *Molecular and Cellular Probes*, 7: 395–404 91993).

Steenken et al.; One–Electron–Reduction Potentials of Pyimidine Bases, Nucleosides and Nucleotides in Aqueous Solution. Consequences for DNA Redox Chemistry, *J. Am. Chem. Soc.*, 114(12): pp. 4701–4709 (1992).

Strobel et al.; Site–Specific Cleavage of a Yeast Chromosome by Oligonucleotide–Directed Triple–Helix Formation, *Science*, pp. 73–75 (Jul. 6 1990).

Strobel et al.; Minor Groove Recognition of the Conserved G–U Pair at the Tetrahymena Ribozyme Reaction Site, *Science*, 267: pp. 675–679 (1995).

Titball et al.; Molecular Cloning and Nucleotide Sequence of the Alpha–Toxin (Phospholiase of C) of *Clostridium perfringens*, *Infection and Immunity*, 57(2): pp. 367–376 (1989).

Tizard et al.; Imaging of DNA Sequences with Chemiluminescence, *Proc. Natl. Acad. Sci.*, 87: pp. 4514–4518 (1990).

Tracy et al.; Dynamics of Rigid and Semirigid Rodlike Polymers, *Annu. Rev. Phys. Chem.*, 43: pp. 525–557 (1992).

Walker et al.; Strand Displacement Amplification–an Isothermal, in vitro DNA Amplification Technique, *Nucleic Acids Research*, 20(7): pp. 1691–1696 (1992).

Walker et al.; Isothermal in vitro Amplification of DNA by a Restriction Enzyme/DNA Polymerase System, *Proc. Natl. Acad. Sci.*, 89: pp. 392–396 (1992).

Wang et al.; Electrochemical Measurements of Oligonucleotides in the Presence of Chromosomal DNA Using Membrane–Covered Carbon Electrodes, *Anla. Chem.*69(19): pp. 4056–4059 (1997).

Waring; Complex Formation Between Ethidium Bromide and Nucleic Acds, *J. Mol. Biol.*, 13: pp. 269–282 (1965).

Hot Prospect for New Gene Amplifier, *Science*, 254: pp. 1292–1293 (1991).

* cited by examiner

ELECTROPOLYMERIZABLE FILM, AND METHOD OF MAKING AND USE THEREOF

CROSS-REFERENCE TO RELATED APPLICATIONS

The instant application is a continuation-in-part of application Ser. No. 08/667,338, filed Jun. 20, 1996; now issued as U.S. Pat. No. 5,871,918, which is a continuation-in-part of application Ser. No. 08/495,817, filed Jun. 27, 1995 (now abandoned); and a continuation-in-part of copending application Ser. No. 08/950,503, filed Oct. 14, 1997, which is a continuation-in-part of co-pending application Ser. No. 08/667,337, filed Jun. 20, 1996; which is a continuation-in-part of application Ser. No. 08/495,817, filed Jun. 27, 1995 (now abandoned), the disclosures of which applications are incorporated herein by reference in their entirety.

BACKGROUND OF THE INVENTION

1. Field of the Invention

The present invention relates to electrodes for detecting nucleic acid hybridization, and to methods of making and using such electrodes.

2. Description of the Related Art

Recent advances in surface modification techniques have facilitated many new methods for bioassay technology, particularly when coupled with sophisticated fluorescent detection technologies. For example, gene expression analysis (Schena, M. et al., *Science* 1995, 270, 467); sequencing of genomic DNA on high-density arrays (Chee, M. et al., *Science*, 1996, 274, 610); and the detection of nucleic acids to identify infectious organisms (Spargo, C. A. et al., *Molecular and Cellular Probes* 1993, 7, 395; Martin, W. J. in *The Polymerase Chain Reaction*; Mullis, K. B.; Ferre, F.; Gibbs, R. A, eds.; 1994, 406–417. Berkhauser, Boston) have the potential for superior selectivity and sensitivity when compared to preexisting culture or immunoassay-based methods. The disclosures of each of the patents and publications referred to herein are incorporated herein by reference. While these systems present significant advancements, they still involve extensive pretreatment steps and the use of expensive fluorescent microscopes.

The electrochemical detection of nucleic acids provides an alternative to fluorescent bioassay techniques that potentially eliminates the need for labeling (Johnston, D. H. et al., *Metal Ions Biol. Syst.* 1996, 33, 297; Johnston, D. H.; Cheng, C. C. et al., *Inorg Chem.* 1994, 33, 6388; Steenken, S. et al., *J. Am. Chem. Soc.* 1997, 119, 617; Johnston, D. H. et al., *J. Am. Chem. Soc.* 1995, 117, 8933; and Johnston, D. H. et al., *J. Phys. Chem.* 1996, 100, 13837).

The invention herein utilizes the discovery that the guanine nucleobases of polymeric DNA produce an array of redox-active labels suitable for ultrasensitive detection that, in conjunction with ultramicroelectrode methods, provide a method for detecting many physiologically relevant nucleic acids prior to PCR amplification. Incorporation of individual microelectrodes into an array allows production of low-cost, rapid-throughput devices with high-density, multiplexed sensor arrays.

Nucleic acids can be detected in solution via catalytic oxidation of guanine bases using $Ru(bpy)_3^{2+}$ as the mediator (Johnston, D. H. et al., *Metal Ions Biol. Syst.* 1996, 33, 297; Johnston, D. H. et al., *Inorg. Chem.* 1994, 33, 6388; Johnston, D. H. et al., *J. Am. Chem. Soc.* 1995, 117, 8933; and Johnston, D. H. et al., *J. Phys. Chem.* 1996, 100, 13837). In solution, $Ru(bpy)_3^{2+}$ exhibits a reversible redox couple at 1.05 V similar to the oxidation potential observed for guanine. Addition of guanine-containing DNA to a solution of $Ru(bpy)_3^{2+}$ leads to catalytic enhancement in the oxidation current according to a two-step mechanism:

$$Ru(bpy)_3^{2+} \rightarrow Ru(bpy)_3^{3+} + e-$$
$$Ru(bpy)_3^{3+} + DNA \rightarrow DNA_{ox} + Ru(bpy)_3^{2+}$$

where $DNA_{ox}$ represents a DNA molecule where guanine has undergone a one electron oxidation.

As set forth in the co-pending parent application (Ser. No. 08/667,338), hybridized DNA may be immobilized on a solid support, and the oxidizing agent then reacted with the hybridized DNA by immobilizing the oxidizing agent on the same solid support and immersing the solid support in a solution under conditions sufficient to permit the oxidation-reduction reaction of the oxidizing agent and a preselected base to occur.

As set forth in co-pending application Ser. No. 08/950,503 (polymer-electrode application), additional schemes in which DNA immobilized onto poly(ethylene terepthalate) or PET membranes and DNA probes attached directly to Indium-Tin Oxide (ITO) electrodes were used for detection of complementary DNA with application as a PCR amplicon bioassay (Napier, M. E. et al., *Langmuir* 1997, 13, 6342; Napier, M. E. et al., H. H. *Bioconjugate Chem.* 1997, 8, 906). In essence, the body of previous investigation has focused on two scenarios: 1) solution mediators with solution DNA and 2) solution mediators with immobilized DNA.

Electrochemical copolymerization has been used to prepare matrices. For example, a DNA matrix has been prepared on an electrode surface via an electrochemically directed copolymerization of pyrrole and oligonucleotides bearing a pyrrole group, together with radiolabeling of the oligonucleotides to detect hybridization (Livache, T. et al., *Nucleic Acids Res.* 1994, 22, 2915; Roget, A. et al., *Nucleosides & Nucleotides* 1995, 14, 943). Also, biosensors have been designed using an electroactive polypyrrole functionalized with an oligonucleotide probe (Korri-Youssoufi, H. et al., *J. Am. Chem. Soc.*, 1997, 119, 7388).

While Livache and Roget use a radioactive label to detect the DNA attached to the electropolymerized film and Korri-Yousoufi monitors the potential of the film itself to indirectly detect DNA hybridization, the invention herein allows for the direct detection of DNA attached to the electropolymerized film via faradaic current from guanine. Thus, the Korri-Yousoufi approach is a potentiometric method, whereas the present method is amperometric. The polymers described herein provide a catalyst for the transfer of electrons from the nucleic acid to the electrode that enables detection of faradaic current, which would be too slow to provide a practical signal without the immobilized mediator. In addition the films of the invention are electrochemically inert in the region 0–0.9 V, whereas the prior polypyrrole films are reactive in this region.

The patent of Yachynych (U.S. Pat. No. 5,540,828) provides a method for making electrodes for protein recognition by electropolymerizing oxidatively. In contrast to Yachynych, the invention herein is used for nucleic acids, in the invention herein polymers are formed reductively rather than oxidatively during polymerization, the invention herein utilizes vinyl-containing polymers, and the metal complex used is both an initiator for electropolymerization and immobilized mediator.

It is therefore an object of the invention to provide surface-modified electrodes for the detection of electron transfer events at potentials near those observed for guanine or other preselected bases in DNA or RNA.

It is a further object of the invention to immobilize a mediator, namely the $Ru^{2+}$ center, for use in the electrochemical detection of guanine bases present in both solution and surface immobilized species.

It is a further object of the invention to use electropolymerization to generate electrodes modified with probes that give greater oxidative current upon hybridization to targets containing larger numbers of preselected bases.

It is a further object of the invention to provide an agent that acts both as initiator for electropolymerization and as a mediator for oxidation of a preselected base.

Other objects and advantages will be more fully apparent from the following disclosure and appended claims.

SUMMARY OF THE INVENTION

The invention herein utilizes a metal complex modified so that polymerization occurs under defined circumstances, and includes an electrode and method of preparing an electrode by electropolymerizing a film on the conductive working surface of an electrode. The electrode is modified by reductive electropolymerization of a thin film of poly[Ru(vbpy)$_3^{2+}$] or poly[Ru(vbpy)$_3^{2+}$/vba] (vbpy=4-vinyl-4'methyl-2,2'-bipyridine and vba=p-vinylbenzoic acid) and the electrode is used for the electrochemical detection of aqueous GMP, poly[G], surface immobilized single-stranded DNA probes, and hybridized DNA or RNA targets. The film is formed from a co-polymer of a mediator such as Ru(vbpy)$_3^{2+}$ and a functionalized moiety having a carboxylate group such as p-vinylbenzoic acid. A DNA probe is attached covalently to the carboxylate group via a carbodiimide reaction followed by amidation of an amino-linked single-stranded DNA. In the presence of these guanine containing moieties, a dramatic enhancement in the oxidative current for the $Ru^{3+/2+}$ couple (present in the polymeric thin film) due to the catalytic oxidation of guanine is observed.

Other objects and features of the inventions will be more fully apparent from the following disclosure and appended claims.

DETAILED DESCRIPTION OF THE INVENTION AND PREFERRED EMBODIMENTS THEREOF

Figure 1:
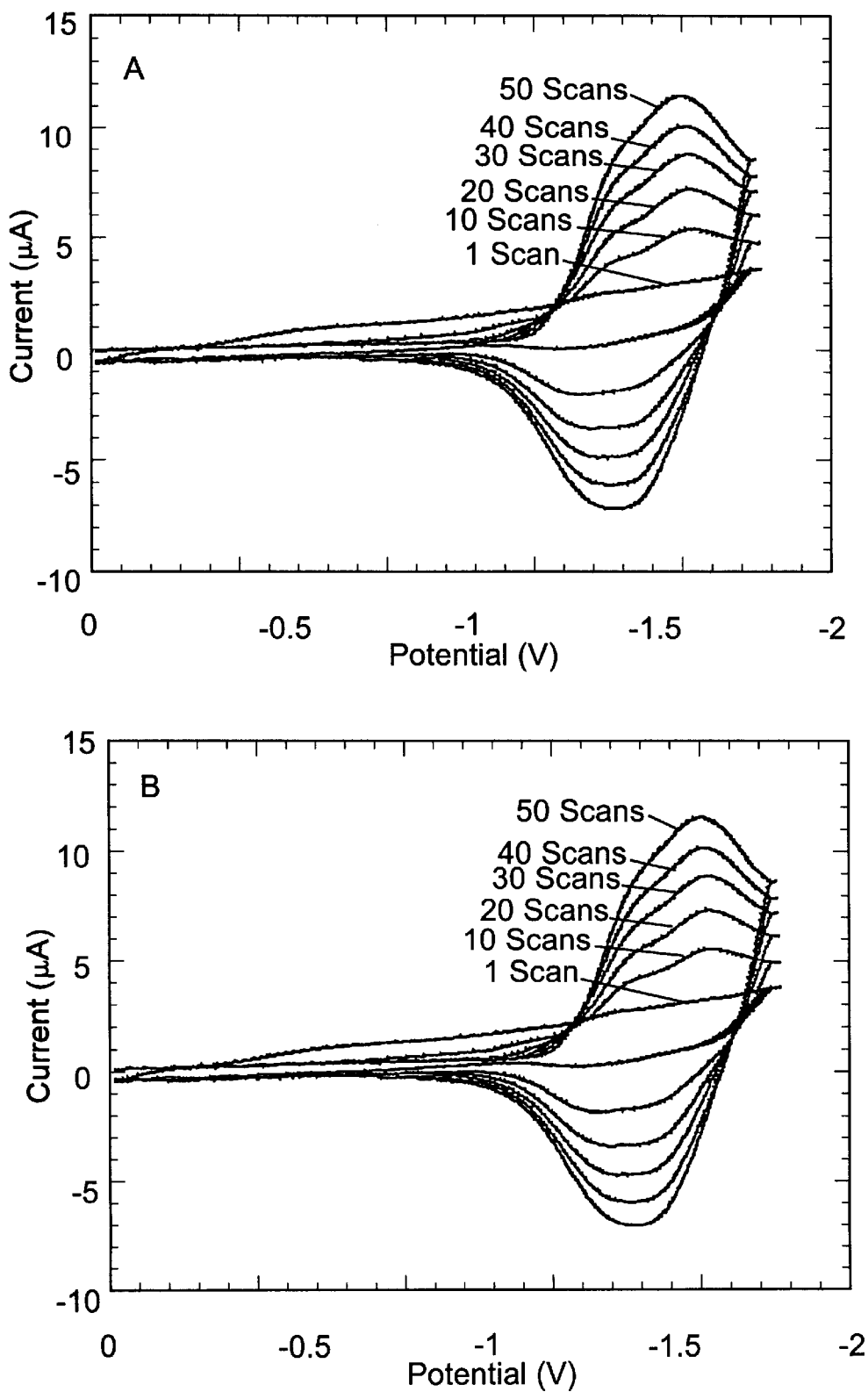
FIGS. 1A and 1B are cyclic voltammograms showing the electropolymerization of (A) poly[Ru(vbpy)$_3^{2+}$], and (B) 5:1 poly[Ru(vbpy)$_3^{2+}$/vba] from an acetonitrile solution containing 0.1 M TBAH onto a glassy carbon electrode (100 mV/s scan rate, Ag/AgNO$_3$ reference). The concentration of Ru(vbpy)$_3^{2+}$ in solution was 0.2 mM.

The invention herein is for a method of making an electropolymerizable film and for the resultant film and the use thereof.

In general, the method of preparing the electrode of the invention having thereon the electropolymerizable film of the invention, comprises:

(a) electropolymerizing a film on an electrode, said film comprising a co-polymer of a metal complex that acts both as an initiator of electropolymerization and an electron-transfer mediator and a functionalized moiety having a carboxylate group; and (b) attaching a DNA probe covalently to the carboxylate group via a carbodiimide reaction followed by amidation of an amino-linked single-stranded DNA.

The electrode of the invention is useful for the electrochemical detection of aqueous GMP, poly[G], and surface immobilized nucleic acids containing a preselected base. It comprises a substrate having a conductive working surface modified by reductive electropolymerization of a thin film. The thin film is selected from the group consisting of poly[Ru(vbpy)$_3^{2+}$] and poly[Ru(vbpy)$_3^{2+}$/vba], wherein vbpy is 4-vinyl-4'-methyl-2,2'-bipyridine and vba is p-vinylbenzoic acid.

In particular, the present invention provides thin polymeric films containing polypyridyl complexes of Ru$^{II}$, generally based on Ru(vbpy)$_3^{2+}$, preferably prepared by reductive electropolymerization onto Pt and glassy carbon electrode surfaces from dilute acetonitrile solutions (vbpy= 4-vinyl-4'-methylbipyridine). These films exhibit an oxidative redox couple at 1.1 V (all potentials vs Ag/AgCl), slightly above that observed for guanine (1.05 V vs. Ag/AgCl) in aqueous solution (Abruna, H. D. et al., *J. Am. Chem. Soc.* 1981, 103, 1; Denisevich, P. et al., *Inorg. Chem.* 1982, 21, 2153). These films should therefore be active catalysts for the electrooxidation of guanine and polymers containing guanine or other preselected bases, such as DNA or RNA.

Further, electropolymerization of a mixture of Ru(vbpy)$_3^{2+}$ and p-vinylbenzoic acid (vba) is used to produce films that contain the ruthenium catalyst and to which amine-appended oligonucleotides can be attached via a carbodiimide reaction that labels the vba. As part of this invention, electrodes modified with films of Ru(vbpy)$_3^2$ are used to catalyze DNA oxidation, and copolymers of Ru(vbpy)$_3^{2+}$ and vba are used to prepare site-specifically assembled loci for DNA detection.

Amplification. Inasmuch as the processes utilizing an electrode having an electropolymerized membrane according to the present invention involve contacting the nucleic acid sample to an oligonucleotide probe to produce a hybridized DNA or RNA, it may be desirable for certain applications to amplify the DNA or RNA prior to contacting with the probe. Amplification of a selected, or target, nucleic acid sequence may be carried out by any suitable means, such as those disclosed and discussed in the co-pending applications.

Detection of nucleic acid. As noted above, the invention herein includes an electrode on which the electropolymerized membrane has been formed, and methods of utilizing this electrode enable detection of hybridized nucleic acid. In this method, a nucleic acid sample is contacted with an oligonucleotide probe to form a hybridized nucleic acid. The oligonucleotide probes which are useful in the methods of the present invention can be any probe comprised of between about 4 or 6 bases up to about 80 or 100 bases or more, more preferably between about 8 and about 30 bases. Oligonucleotide probes may be prepared having any of a wide variety of base sequences according to techniques which are well known in the art. Suitable bases for preparing the oligonucleotide probe may be selected from naturally occurring nucleotide bases such as adenine, cytosine, guanine, uracil, and thymine; and non-naturally occurring or "synthetic" nucleotide bases such as 8-oxo-guanine, 6-mercaptoguanine, 4-acetylcytidine, 5-(carboxyhydroxyethyl)uridine, 2'-O-methylcytidine, 5-carboxymethylamino-methyl-2-thiouridine, 5-carboxymethylaminomethyluridine, dihydrouridine, 2'-O-methylpseudouridine, D-galactosylqueosine, 2'-O-methylguanosine, inosine, 7-deazaguanine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, D-mannosylqueosine, 5-methoxycarbonylmethyluridine, 5-methoxyuridine, 2-methylthio-N6-isopentenyladenosine, N-((9-D-ribofuranosyl-2-methylthiopurine-6-yl)carbamoyl)threonine, N-((9-D-ribofuranosylpurine-6-yl)N-methylcarbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 5-methyluridine, N-((9-D-ribofuranosylpurine-6-yl)carbamoyl)threonine, 2'-O-methyl-5-methyluridine, 2'-O-methylurdine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates (for example, every other one of the internucleotide bridging phosphate residues may be modified as described). The oligonucleotide may be a "peptide nucleic acid" such as described in P. Nielsen et al., 1991, *Science* 254, 1497–1500. The only requirement is that the oligonucleotide probe should possess a sequence at least a portion of which is complementary to a known portion of the sequence of the target nucleic acid. It may be desirable in some applications to contact the nucleic acid sample with a number of oligonucleotide probes having different base sequences (e.g., where there are two or more target nucleic acids in the sample, or where a single target nucleic acid is hybridized to two or more probes in a "sandwich" assay).

Preselected base. After hybridization, the hybridized nucleic acid that is attached to the electropolymerized membrane may be reacted with a suitable mediator that is immobilized to the membrane and is capable of oxidizing a preselected base in an oxidation-reduction reaction. The preselected base can be any naturally occurring or synthetic nucleotide base which undergoes oxidation upon reaction with the selected mediator. The preselected base should exhibit unique oxidation rates when paired with each of the four naturally occurring bases. Generally, bases whose 5'-mononucleotides (e.g., the 5'-deoxyribonucleotide or 5'-ribonucleotide) exhibit rate constants above $10^4 M^{-1}s^{-1}$ can be detected using the catalytic reaction. Examples of suitable preselected bases include but are not limited to guanine, adenine, 8-oxo-guanine, and 8-oxo-adenine, 8-bromo-guanine, xanthine, pseudouridine, 6-mercaptoguanine, 8-mercaptoguanine, 2-thioxanthine, 6-thioxanthine, 6-mercaptopurine, 2-amino-6-carboxymethylmercaptopurine, 2-mercaptopurine, 6-methoxypurine, 2-acetylamino-6-hydroxypurine, 6-methylthio-2-hydroxypurine, 2-dimethylamino-6-hydroxypurine, 2-hydroxypurine, 2-aminopurine, 6-amino-2-dimethylallyl-purine, 2-thioadenine, 8-hydroxyadenine, 8-methoxyadenine. Typically, the preselected base is selected from the group consisting of guanine, adenine, 6-mercaptoguanine, 8-oxo-guanine, and 8-oxo-adenine, with guanine being the currently preferred naturally occurring preselected base and 8-oxoguanine the currently preferred synthetic preselected base.

Mediator. The mediator that may be used to enable electron transfer and to initiate the electropolymerization is one that (a) has a reversible oxidative redox couple and is capable of oxidizing a preselected base, (b) has a substituent capable of undergoing electropolymerization at potentials other than that of the oxidative redox couple, and (c) exhibits a different redox couple that can be used to initiate electropolymerization. For example, the Ruthenium$^{2+}$(2,2'-bipyridine)$_3$(Ru(vbpy)$_3^{2+}$ where vbpy=4-vinyl-4'methyl-2,2'-bipyridine) complex exhibits an oxidative redox couple at approximately 1.0 V, which can mediate the oxidation of guanine, the vinyl group on the bpy ligand can be used for polymerization, and the complex exhibits a reductive redox couple at −1.1 V that can be used to initiate the polymerization. Mediators that meet these criteria include metal complexes containing vinyl-substituted polypyridyl ligands that exhibit both oxidative and reductive redox couples.

Detection of oxidation-reduction reaction. The occurrence of the oxidation-reduction reaction may be detected using an electropolymerized membrane on an electrode in accord with the present invention to observe a change in the electronic signal which is indicative of the occurrence of the oxidation-reduction reaction. Typically, an electrode modified with the electropolymerized film containing the mediator and to which nucleic acid is immobilized is brought into contact with a solution that is also in contact with a reference and auxiliary electrode (with most of the current passing through the auxiliary electrode). Similarly, suitable reference electrodes will also be known in the art and include, for example, silver/silver chloride electrodes.

The detection of the electronic signal associated with the oxidation-reduction reaction permits the determination of the presence or absence of hybridized nucleic acid. The step of determining the presence or absence of hybridized nucleic acid typically includes (i) measuring the reaction rate of the oxidation-reduction reaction, (ii) comparing the measured reaction rate to the oxidation-reduction reaction rate of the transition metal complex with single-stranded nucleic acid, and then (iii) determining whether or not the measured reaction rate is essentially the same as the oxidation-reduction reaction rate of the transition metal complex with single-stranded nucleic acid. The step of measuring the reaction rate may be carried out by any suitable means. For example, the relative reaction rate may be determined by comparing the current at the same scan rate, probe concentration, target concentration, mediator, buffer, temperature, and/or electrochemical method.

The oxidation-reduction reaction rate may be measured according to suitable means known to those skilled in the art. Typically, the oxidation-reduction reaction rate is measured by measuring the electronic signal associated with the occurrence of the oxidation-reduction reaction. For example, the electronic signal associated with the oxidation-reduction reaction may be measured by providing a suitable apparatus in electronic communication with an electrode coated with an electropolymerized membrane as disclosed herein. A suitable apparatus is a potentiostat capable of measuring the electronic signal which is generated so as to provide a measurement of the oxidation-reduction reaction rate of the reaction between the hybridized nucleic acid and the mediator.

The electronic output may be characteristic of any electrochemical method, including cyclic voltammetry, normal pulse voltammetry, chronoamperometry, and square-wave voltammetry, with cyclic voltammetry being the currently preferred form. A computer as is known in the art may be used for controlling the use of the electrode and for recording results of such use. The method most frequently used to electropolymerize membranes on ITO electrodes according to the invention is cyclic voltammetry. In cyclic voltammetry, the potential of the electrochemical system is varied linearly from an initial potential (0–800 mV) to a final potential (1300–1800 mV). When the final potential is reached, the scan direction is reversed and the same potential range is swept in the opposite direction. The potential is varied at a constant scan rate (25 mv/s to 50 V/s). For the majority of experiments, the initial potential is set at 0 mV and the final potential is sufficient to effect the oxidation of the mediator. The current preferred scan rate is 50 mV/s with a switching potential of 1.4 V. The current is collected at each potential and the data are plotted as a current versus potential spectra.

As an alternative to cyclic voltammetry, potential step methods such as chronocoulometry or chronoamperometry, may be used to analyze electropolymerizable membranes of the invention. In chronocoulometry, a step potential is applied. Starting at the initial potential (0 mV–800 mV), the electrochemical system is stepped directly to the final potential (1100 mV–1600 mV). The electrochemical system is held at the final potential for some specified period of time (50 $\mu$s to 10 s) and the charge is collected as a function of time. Although not currently done, if desired, the potential can be stepped back to the initial potential and the charge can be collected at the initial potential as a function of time. In chronoamperometry, the electrochemical system is stepped from an initial potential (0 mV–800 mV) directly to a final potential (1000–1500 mV) for some specified period of time (50 $\mu$s to 10 s) and the current is collected as a function of time. If desired, the potential can be stepped back to the initial potential, and the current can be collected at the initial potential as a function of time.

In the methods described in co-pending Ser. No. 08/667, 337, metal complexes are used to obtain an electrochemical current from single- and double-stranded nucleic acids. Preselected bases such as guanine give an electrochemical signal, and this signal is much weaker for double-stranded DNA. Such methods advantageously exhibit high structural sensitivity, and can resolve a single base mismatch. Such methods are therefore particularly advantageous for the sequencing of DNA. However, two drawbacks of such methods are that: (a) there is a negative signal on going from the probe strand to the hybrid, and (b) the number of preselected bases is limited which limits the signal. The techniques set forth herein provide solutions to these problems. In addition, these techniques are particularly useful for diagnostic assays, and are particularly useful for the quantitative detection of nucleic acids.

In view of the foregoing, also disclosed herein and in Ser. No. 08/667,337, is a method of detecting the presence or absence of a target nucleic acid in a test sample suspected of containing the same, wherein the target nucleic acid contains at least one preselected base. In this method, the preselected base is located on the target nucleic acid, rather than on the oligonucleotide probe.

Test samples. The method may be carried out on a test sample containing the target nucleic acid. Any test sample suspected of containing the target nucleic acid may be used, including, but not limited to, tissue samples such as biopsy samples and biological fluids such as blood, sputum, urine and semen samples, bacterial cultures, soil samples, food samples, etc. The target nucleic acid may be of any origin, including animal, plant or microbiological (e.g., viral, prokaryotic, and eukaryotic organisms, including bacterial, protozoal, and fungal, etc.) depending on the particular purpose of the test. Examples include surgical specimens, specimens used for medical diagnostics, specimens used for genetic testing, environmental specimens, food specimens, dental specimens and veterinary specimens. The sample may be processed or purified prior to carrying out the instant method in accordance with techniques known or apparent to those skilled in the art; and nucleic acids therein may be digested, fragmented, and/or amplified (see above) prior to carrying out the instant method, if so desired.

Method of detection. Detection of a preselected base on a target nucleic acid using an electrode with an electropolymerized membrane according to the invention herein comprises (a) contacting the test sample to an oligonucleotide probe that specifically binds to the target nucleic acid to form a hybridized nucleic acid; (b) detecting the presence or absence of the oxidation-reduction reaction associated with the hybridized nucleic acid; and (c) determining the presence or absence of the target nucleic acid in the test sample from the detected oxidation-reduction reaction at the preselected base. The oligonucleotide probe may be immobilized on a solid support (the electropolymerized film) to facilitate separating the test sample from the hybridized nucleic acid, with the separating step occurring prior to the detecting step (e.g., between steps (a) and (b) or betweens steps (b) and (c)). Alternatively, the oligonucleotide probe may be provided free in solution, and other means provided to separate the hybridized nucleic acid from the sample (e.g., by a mediator nucleic acid that binds to the oligonucleotide probe, or by a biotin-avidin binding interaction, where biotin is bound to the oligonucleotide probe and avidin is immobilized on a solid support). The oxidation-reduction reaction, and any step up to the detection step may be done on the electropolymerized film before or after the film is brought into contact with the conductive working surface of the substrate.

Preferably, the target nucleic acid contains at least ten more of the preselected base than does the oligonucleotide probe, or more preferably at least 50 or 100 more of the preselected base than does the oligonucleotide probe. A larger current enhancement is advantageously obtained when the target nucleic acid contains many more of the preselected base than does the oligonucleotide probe.

Optionally, but preferably, the oligonucleotide probe is free of the preselected base, or is at least essentially free of the preselected base (i.e., contains sufficiently less of the preselected base so that signal from probe does not interfere with or is not mistaken as a signal from the target nucleic acid). Where a sequence of naturally occurring bases that will conveniently hybridize to the target nucleic acid is not available, the strategy of employing alternate bases that are redox inactive (discussed below) may be employed.

The target nucleic acid is preferably longer than the oligonucleotide probe, and at least one of the preselected bases is "overhanging", i.e., not hybridized to the oligonucleotide probe in the hybridized nucleic acid. Preferably, at least 10, 50, or 100 of the preselected bases are "overhanging" bases, thereby providing substantial amplification of the electrochemical signal detected.

For example, an oligonucleotide probe that does not contain any guanine residues (e.g., only A, T, and C) may be chosen. The cyclic voltammogram of Ru $(bpy)_3^{2+}$ in the presence of this strand is very similar to that without the oligomer. This probe is then hybridized to a target strand that contains guanines in either the overlapping base-paired regions and/or in overhanging regions if the target nucleic acid is longer than the oligonucleotide probe. Because multiple guanines are detected, the signal is amplified relative to the number of hybrids formed. In a case where a genomic DNA or RNA is the target strand, large numbers of overhanging guanines are encountered, which would give tremendous signal amplification.

For example, in one preferred embodiment, the assay for the preselected base on the target strand involves immobilization of the (preferably redox-silent) probe strand on the film oriented close to the electrode surface, which provides a low background signal when scanned. The electropolymerized film is then contacted with a solution of the target strand, which contains the preselected base. If hybridization occurs, the target strand will now be in close proximity to the electrode, and a current enhancement will be detected. This method is particularly well suited to the quantitative detection of nucleic acids, since the greater the extent of hybridization, the greater the quantity of preselected base on the surface, and the greater the electrochemical signal.

Alternate Bases That Are Redox Inactive. An alternate base may be used that would substitute for guanine (i.e., a base that, like guanine, has a greater binding affinity for cytosine than do other bases in a nucleic acid duplex) in the probe strand but would not be oxidized by the mediator under the applicable reaction conditions. When the preselected base in the target nucleic acid is guanine and the target nucleic acid also contains cytosine (which ordinarily bonds with guanine in the probe), then the probe contains an alternate base that bonds to cytosine in the hybridized nucleic acid. The alternate base may, for example, be inosine. Inosine is three orders of magnitude less reactive than guanine. The reacting step typically comprises reacting the transition metal complex with the nucleic acid under conditions sufficient to effect the selective oxidation of the preselected base without oxidizing the alternate base.

Thus, a method of detecting a target nucleic acid, where the target nucleic acid contains at least one preselected base and the probe or capture nucleic acid contains alternate redox inactive bases comprises: (a) contacting the target nucleic acid to a complementary nucleic acid that specifically binds to the target nucleic acid to form a hybridized nucleic acid; (b) detecting the oxidation-reduction reaction; and (c) determining the presence or absence of the nucleic acid from the detected oxidation-reduction reaction at the preselected base.

The features of the present invention will be more clearly understood by reference to the following examples, which are not to be construed as limiting the invention.

EXAMPLES

Example 1

Reagents and DNA. Inorganic reagents used in these experiments were of analytical grade or higher. The inorganic complex, $[Ru(vbpy)_3](PF_6)_2$, was prepared using standard literature procedures (Abruna, H. D. et al., *J. Am. Chem. Soc.* 1981, 103, 1). The sensing probe, $CpFe(C_5H_4-C_2H_4NH_2)$ was synthesized by a standard $LiAlH_4$ reduction of the cyano-substituted ferrocene, $CpFe(C_5H_4-CH_2CN)$ followed by work-up from diethyl ether. Water-soluble carbodiimide (WSC, 1-(3-dimethylaminopropyl)-3-ethylcarbodiimide hydrochloride), DCC (dicyclohexylcarbodiimide), TBAH (tetrabutylammonium hexafluorophosphate), NHS (N-hydroxysuccinimide), GMP (guanosine monophosphate, disodium salt), poly[G], and vba were purchased from Aldrich (Milwaukee, Wis.) and used as received. Two recrystallizations of vba from 50% ethanol were done prior to electrochemical experiments to insure purity. MES (2-Morpholinoethanesulfonic acid sodium salt and 2-Morpholinoethanesulfonic acid monohydrate) were purchased from Fluka (New Ulm, Switzerland). $Na_2HPO_4$, $NaH_2PO_4$, NaCl, and acetonitrile were obtained from Mallinckrodt (Phillipsburg, N.J.). The acetonitrile was dried over activated molecular sieves prior to use in electropolymerization experiments. Synthetic oligonucleotides were synthesized by the Department of Pathology, The University of North Carolina at Chapel Hill, and purified using Amicon micron 3 concentrators with a cutoff of 3000 molecular weight. Water was obtained from a Milli-Q Plus purification system (Millipore, Bedford, Mass.). Glassy carbon electrodes (GCE's, 3 mm diameter) were purchased from BAS (West Lafayette, Ind.) and polished prior to use.

Example 2

Electrochemical Analysis. Cyclic voltammograms were collected using a PAR 273A potentiostat/galvanostat. Experiments done in acetonitrile used a two compartment voltammetric cell equipped with a glassy carbon working electrode, a platinum mesh counter electrode, and a $Ag/AgNO_3$ reference electrode. Aqueous experiments were carried out using a single compartment voltammetric cell equipped with a glassy carbon working electrode, platinum wire counter electrode, and a Ag/AgCl reference electrode. Prior to use, all GCEs were thoroughly polished with METADI diamond polishing compound (Buehler, Lake Bluff, Ill.) and $Al_2O_3$ (0.5 µm in $H_2O$) on a felt polishing platform. The electrodes were then rinsed several times with Milli-Q water and dry acetonitrile immediately before use. Electropolymerization reactions were done by filling the working electrode compartment with 3.5 ml of a 0.2 mM $[Ru(vbpy)_3](PF_6)_2$, 0.1 M TBAH acetonitrile solution and scanning reductively 10 times between −0.9 and −2.0 V with a 100 mV/s scan rate. These solutions must be thoroughly dried and degassed prior to reductive scanning, and the reference electrode compartment must be filled with 0.1 M TBAH in acetonitrile. For formation of vba-doped films, a 5:1 [Ru(vbpy)$_3$](PF$_6$)$_2$ to vba solution ratio was found to produce films with the greatest reproducibility. Electrochemical oxidation of aqueous GMP, poly[G], and attached DNA probes was done in a 50 mM, pH 7.0 phosphate buffer, scanning positively from 0.0 to 1.4 V at a 50 mV/s scan rate.

Example 3

Attachment of DNA to Film-Modified Electrodes. Attachment of the DNA probe was carried out using a standard amidation procedure in which the surface carboxyl groups (present in the film as vba spacers) are activated using well understood carbodiimide chemistry and subsequently undergo amidation reactions with amino-linked single-stranded DNA (Millan, K. M. et al., *Anal. Chem.* 1993, 65, 2317; Sehgal, D. et al., *Anal. Biochem.* 1994, 218, 87). After electropolymerization of poly[Ru(vbpy)$_3^{2+}$/vba] onto a GCE, the electrode was carefully rinsed with acetonitrile to remove residual [Ru(vbpy)$_3$](PF$_6$)$_2$, vba, and TBAH. The electrode was then inverted, and a 50 μl drop of EDC/NHS solution (made by dissolving 10 mg EDC and 1 mg NHS in 1.0 ml Milli-Q water) was carefully placed on the electrode surface. The electrode was covered with an inverted beaker for 30 min. The treated GCE was then rinsed numerous times with water and carefully blotted dry. Again, the electrode was inverted, and a 25 μl drop of a pH buffered, 5 μM DNA probe solution (20-mer, poly[dG] with a 3'-(CH$_2$)$_6$ NH$_2$ linking group) was placed on the electrode face. The electrode was allowed to rest covered and undisturbed for 90 min before rinsing with an 800 mM NaCl, 50 mM phosphate buffer (pH 7.0) solution. A high salt solution was necessary for this rinsing step to disrupt any electrostatic interactions between the polymer surface and non-covalently bound DNA.

Example 4

Quantification of Immobilized Probe. The 20-mer probe was 5'-$^{32}$P-labeled using T4 polynucleotide kinase and γ-$^{32}$P-ATP (6000 Ci/mmol) according to standard procedures (Maniatis, T. et al. in *Molecular Cloning: A Laboratory Manual.* 1989. Cold Spring Harbor Press). Unreacted ATP was removed from the labeled probe using a Stratagene NucTrap column using standard techniques. The radiolabeled probe was attached using the identical procedure described for non-labeled probe using a stock DNA solution (270 μl total volume) containing 5 pmol labeled probe diluted to 5 μM with non-labeled probe in either pH 6.5 MES or pH 9.0 carbonate buffer solution. After immobilization, the probe-modified film was mechanically removed from the electrode face by rubbing the polymer onto a piece of filter paper. Control films were obtained in an identical manner by excluding the EDC/NHS amidation step of the reaction. The radioactivity of these samples was then determined in triplicate using both liquid scintillation and phosphorimaging techniques.

Example 5

Figure 7:
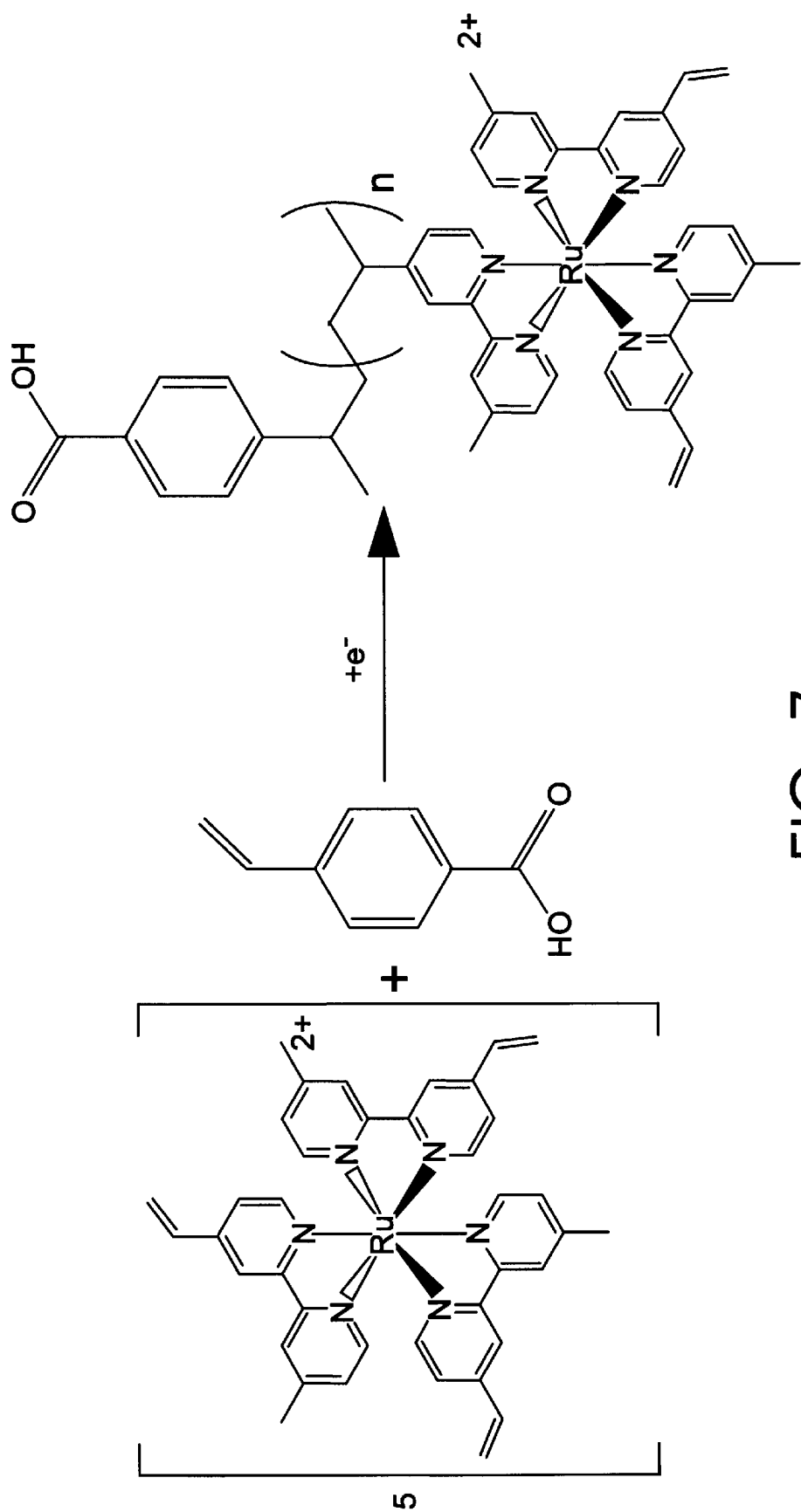
FIG. 7 is a representation of Scheme 1 which shows formation of copolymer upon electropolymerization.

Preparation of polymer-modified electrodes. Electropolymerization of poly[Ru(vbpy)$_3^{2+}$] films onto electrode surfaces has been well characterized and films can be readily fabricated in reproducible thicknesses using varied scan times and scan rates as discussed herein. FIGS. 1A and 1B show polymer growth for both a simple ruthenium-containing film, poly[Ru(vbpy)$_3^{2+}$], and a film doped with the carboxyl-containing vba group, poly[Ru(vbpy)$_3^{2+}$/vba]. Scheme 1 shown in FIG. 7 shows formation of copolymer upon electropolymerization. As has been previously demonstrated, poly[Ru(vbpy)$_3^{2+}$] films can be reversibly oxidized in media where the Ru$^{3+}$ is stabilized upon formation (i.e. dry acetonitrile and strong acid solutions) (Abruna, H. D. et al., *J. Am. Chem. Soc.* 1981, 103, 1; Denisevich, P. et al., *Inorg. Chem.* 1982, 1, 2153). Identical behavior was also observed during these studies for poly[Ru(vbpy)$_3^{2+}$/vba] doped films.

Example 6

Figure 2:
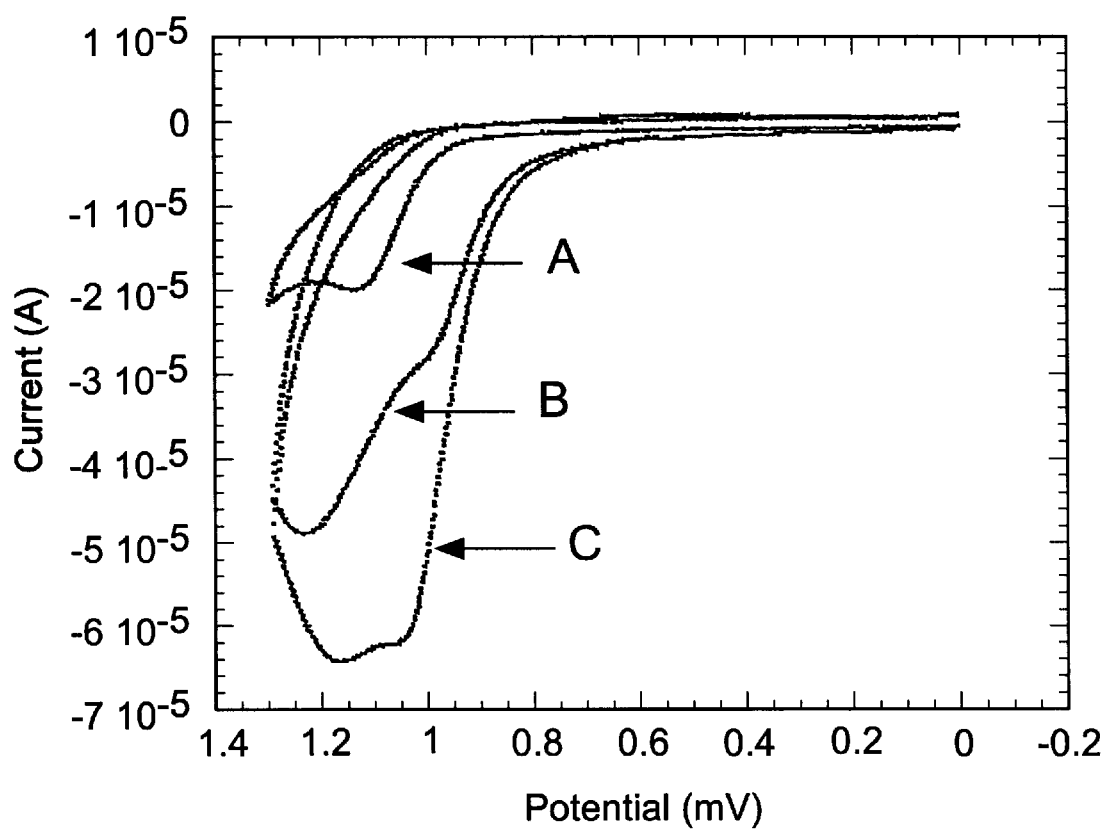
FIG. 2 shows cyclic voltammograms showing the oxidation of guanosine monophosphate (GMP) using (A) an unmodified GCE and a poly[Ru(vbpy)$_3^{2+}$] film-modified GCE in the (B) absence and (C) presence of GMP (50 mV/s scan rate, Ag/AgCl reference, 50 mM, pH 7.0 phosphate buffered solution)
Figure 3:
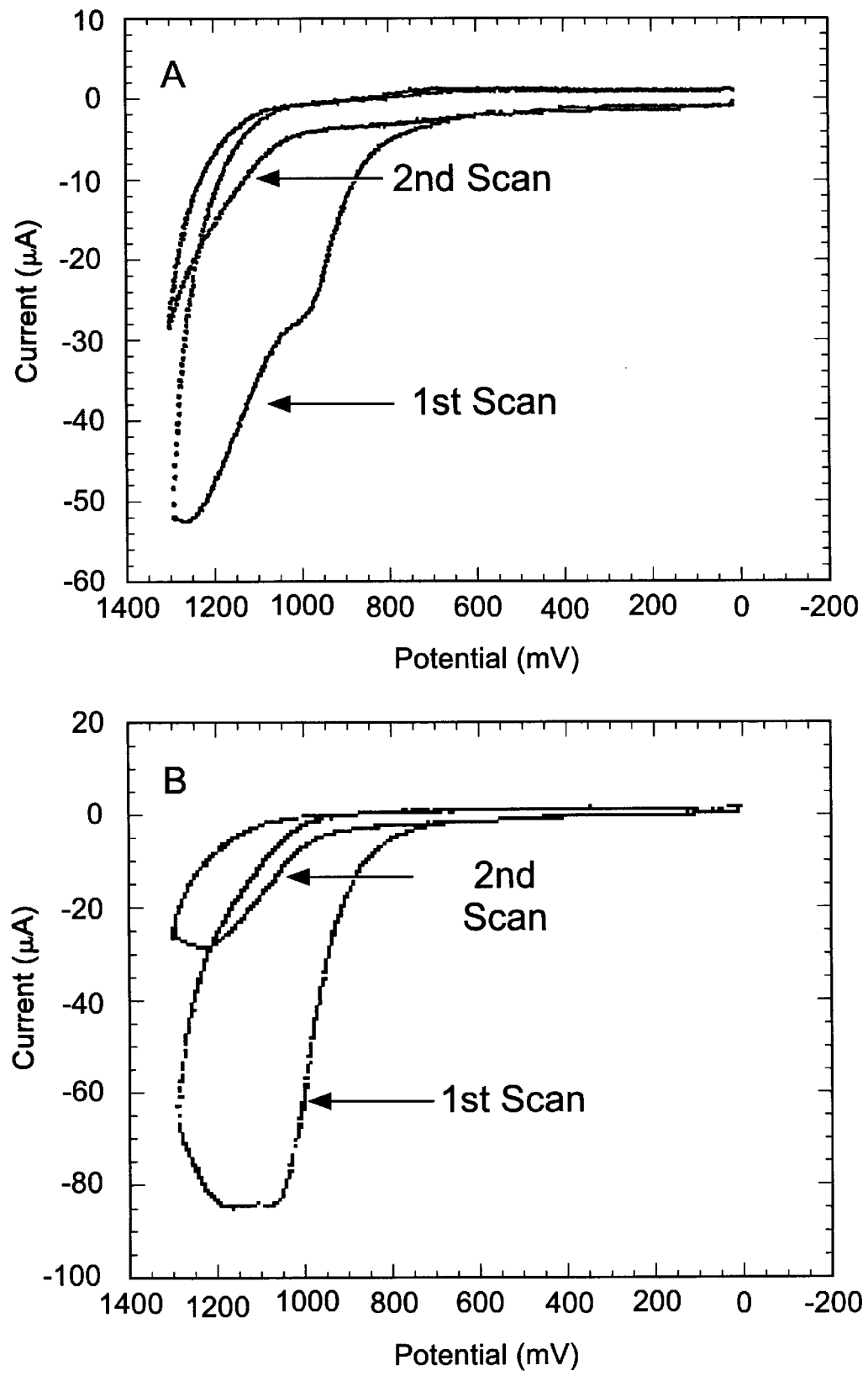
FIG. 3A shows the first and second oxidative scans of a poly[Ru(vbpy)$_3^{2+}$] film-modified GCE and FIG. 3B shows the first and second oxidative scans of a poly[Ru(vbpy)$_3^{2+}$] film-modified GCE in the presence of GMP (50 mV/s scan rate, Ag/AgCl reference, 50 mM, pH 7.0 phosphate buffered solution).
Figure 4:
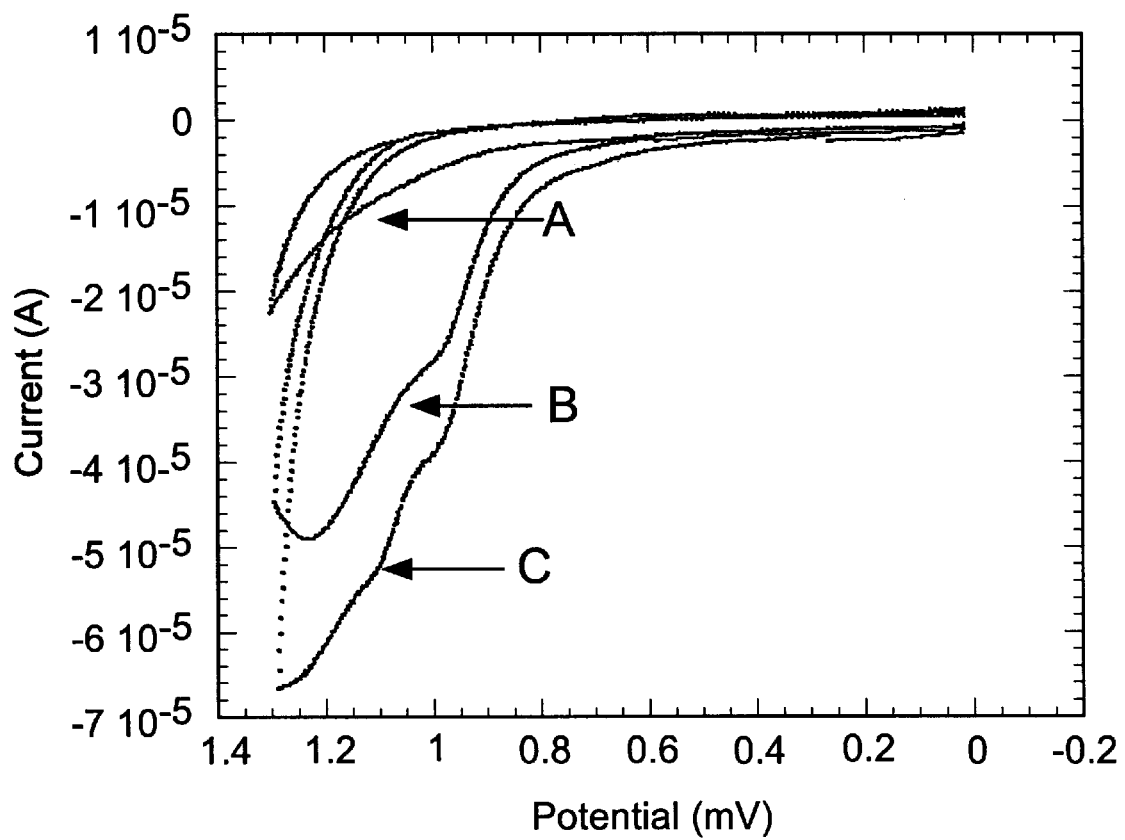
FIG. 4 shows cyclic voltammograms showing the oxidation of poly[G] using (A) an unmodified GCE and a poly [Ru(vbpy)$_3^{2+}$] modified GCE in (B) the absence and (C) the presence of poly[G](50 mV/s scan rate, Ag/AgCl reference, 50 mM, pH 7.0 phosphate buffered solution).

Detection of GMP and poly[G]. GCE's modified with a poly[Ru(vbpy)$_3^{2+}$] film were scanned oxidatively in the presence and absence of GMP and poly[G] in a pH 7.0, phosphate buffer solution (FIGS. 2, 3, and 4). In FIG. 2, exposure of an unmodified GCE to a 1.0 mM GMP solution produces oxidation currents significantly smaller than those of polymer-modified electrodes. Even subtraction of background current produced by oxidation of the polymer itself shows positive current indicative of a catalytic electron-transfer process. Further support for the proposed catalytic mechanism is shown in FIGS. 3A and 3B. The voltammogram in FIG. 3 demonstrates the stability of the film in the presence of the electron donor GMP. In the absence of a suitable concentration of electron donor, complete decomposition of ruthenium centers in the film is observed (FIG. 3A). However, when GMP is present in solution, the oxidized Ru$^{3+}$ present in the rigid film are sometimes able to abstract an electron from a proximal GMP molecule prior to rapid decomposition. This effect is evidenced by the presence of a GMP oxidation wave upon completion of a second oxidative scan in GMP solution (FIG. 3B). The GMP molecules are too large to diffuse through holes produced upon decomposition loss of Ru$^{3+}$ from the film. In an experiment where a poly[Ru(vbpy)$_3^{2+}$] film was oxidized in the absence of GMP solution followed by a second oxidative scan in a GMP containing solution, a voltammogram identical to that for the second scan in FIG. 3A was observed. A separate observation was noted that dilution of GMP solutions by two orders of magnitude (0.01 mM) had little effect on the amount of current produced during the first oxidative scan. This effect can be attributed to the electrostatic attraction between the positively charged polymer surface and the anionic GMP. This presumably creates a local concentration at the electrode surface that is much greater than that of the bulk solution.

Cyclic voltammograms of the oxidation of poly[G] using clean and poly[Ru(vbpy)$_3^{2+}$] modified electrodes are shown in FIG. 4 and demonstrate two definable characteristics. First, no electrochemical oxidation of poly[G] occurs in the absence of a poly[Ru(vbpy)$_3^{2+}$] film. Due to the slow diffusion of such a large polymer to the film (relative to the cyclic voltammetric time scale), oxidation of the poly[G] is undetectable. However, in the presence of a poly[Ru(vbpy)$_3^{2+}$] treated electrode, a current enhancement over that observed for poly[Ru(vbpy)$_3^{2+}$] oxidation alone is seen. Again, the electrostatic attraction of the cationic polymer surface likely aids the diffusion of the large poly[G] molecule to the electrode surface where Ru-mediated catalytic oxidation can occur.

Example 7

Figure 5:
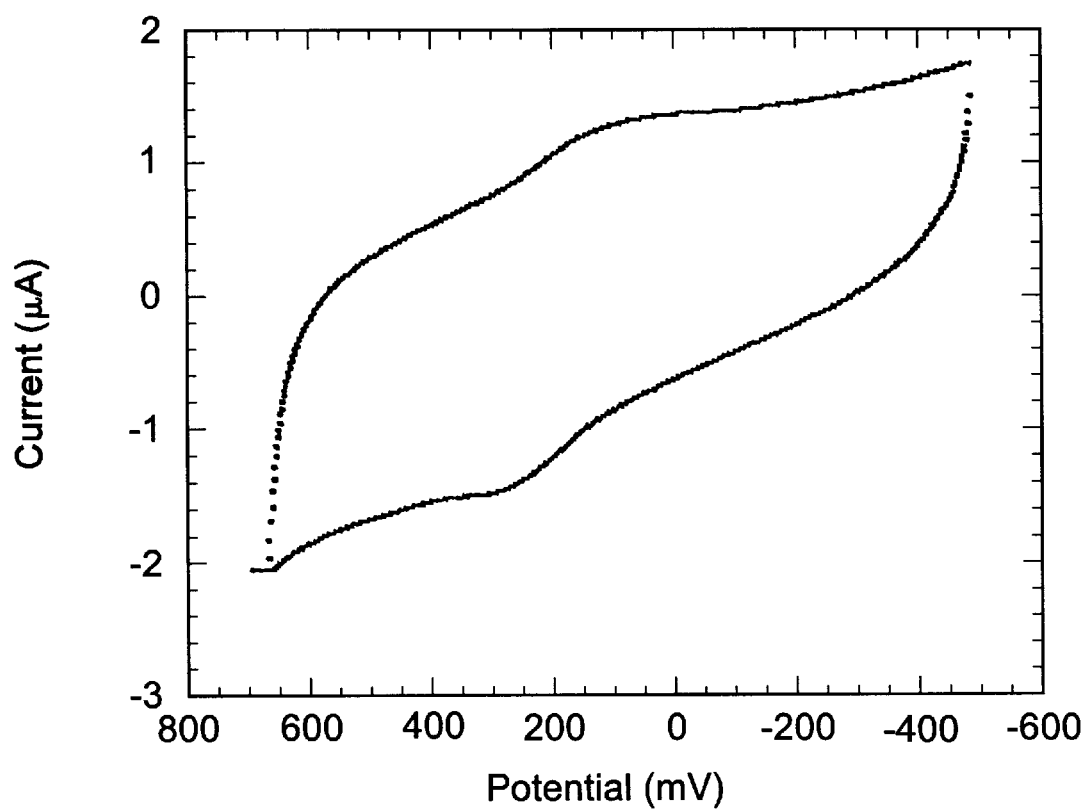
FIG. 5 is a cyclic voltammogram of a 5:1 poly[Ru(vbpy)$_3^{2+}$] film-modified GCE with immobilized CpFe(C$_5$H$_4$—NH$_2$) (50 mV/s scan rate, Ag/AgNO$_3$ reference, 0.2 mM Ru$^{2+}$, 0.1 M TBAH solution).

Detection of immobilized probes. The amino-modified ferrocene probe (CpFe(C$_5$H$_4$—C$_2$H$_4$NH$_2$)) was attached to a 10-scan, poly[Ru(vbpy)$_3^{2+}$/vba] modified electrode (FIG. 1B), using the same protocol for aqueous amidation with DCC in methylene chloride substituted for EDC. This activation step was then followed by amidation of the ferrocene amino-group (FIG. 5) rendering the ferrocene molecule surface-immobilized. Measurable current was observed at 0.2 V in a 0.1M TBAH, acetonitrile solution, representative of the presence of the $Fe^{2+}/Fe^{3+}$ ferrocene couple on the modified electrode surface.

Figure 8:
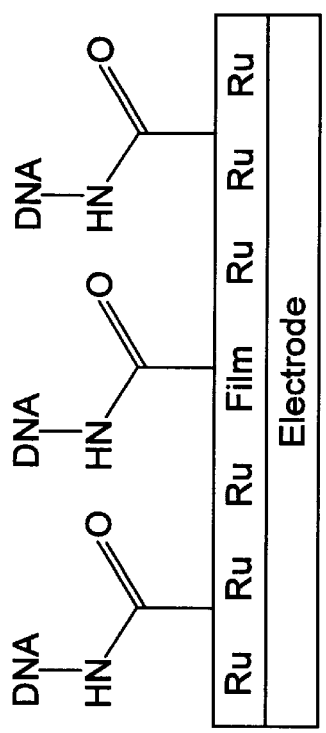
FIG. 8 is a representation of Scheme 2 which shows immobilization of the amino-linked, DNA probe to the surface.
Figure 8:
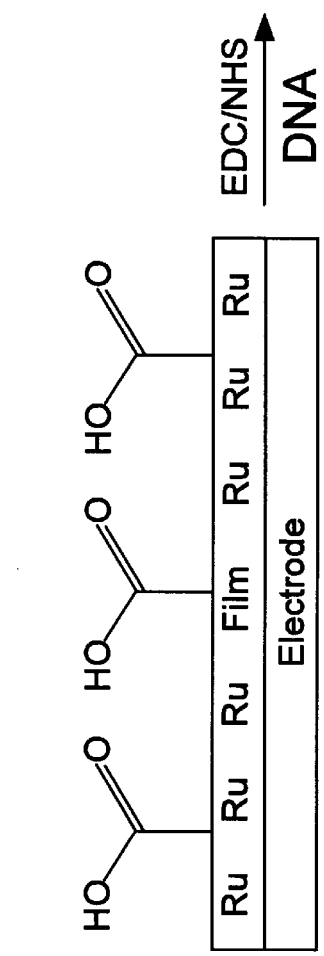

Immobilization of the amino-linked DNA probe to the surface was performed (Scheme 2 shown in FIG. 8). Immobilization reactions were done at two different pH values (6.5 and 9.0) to chemisorb the probe in two distinctly different fashions. At higher pH, amidation preferentially occurs at the primary amine of the attached —$(CH_2)_6NH_2$ group as opposed to any native endogenous amine groups on the purine and pyrimidine rings of DNA. Amidation of these native-amine groups would produce electrode surfaces where DNA would be attached not only at the amino-linking group, but at several of the native amines as well producing a surface with fewer probe molecules 'stapled' to the surface (Scheme 3). Using this assumption, it was thought that amidation at pH 9.0 would produce films containing greater numbers of immobilized DNA probe strands as stacking would be maximized and native amine amidation (or stapling) would be minimized.

Figure 6:
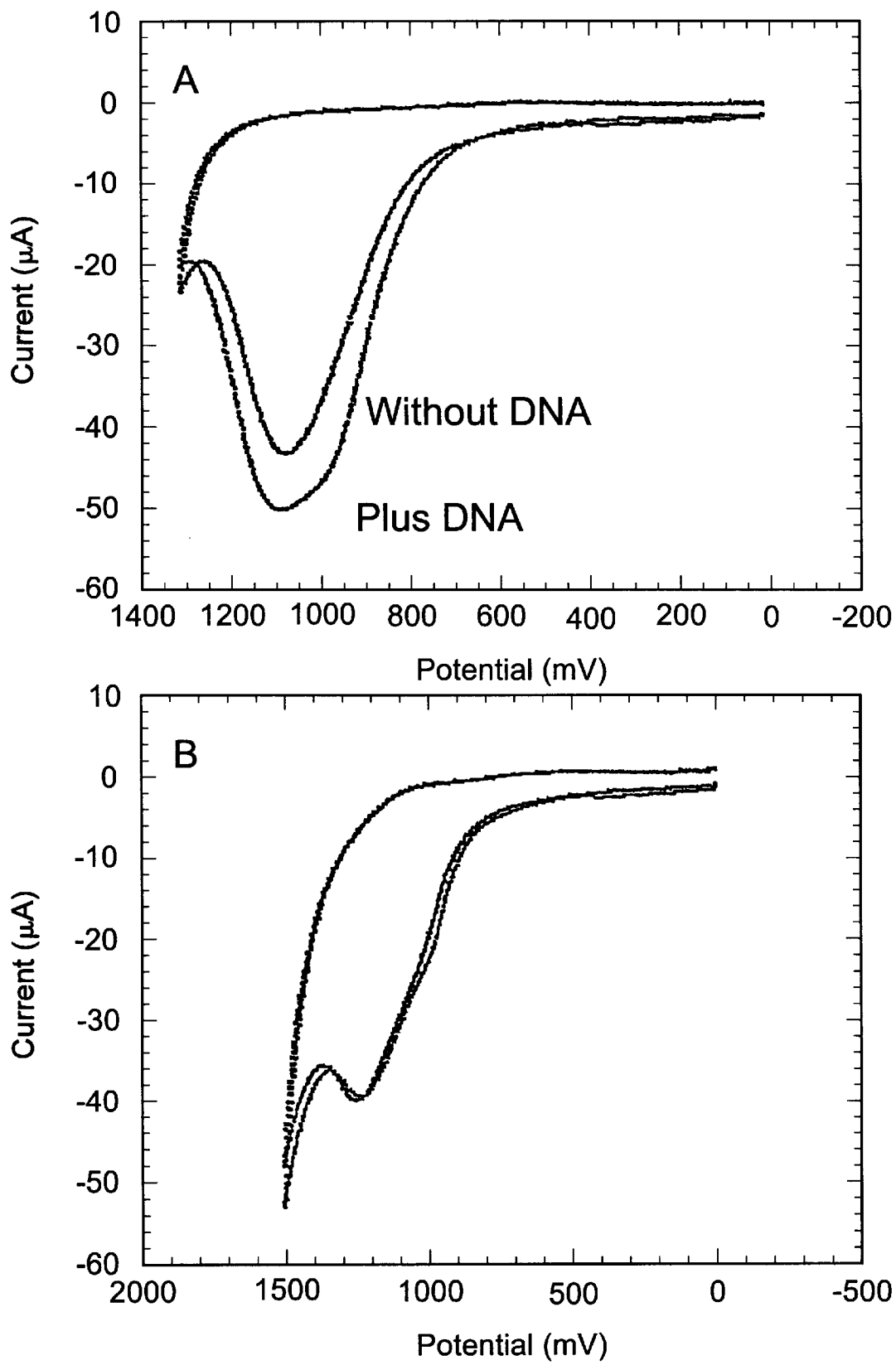
FIG. 6 shows cyclic voltammograms of (A) a 5:1 poly [Ru(vbpy)$_3^{2+}$/vba] film-modified GCE with 20-mer poly [dG] immobilized at pH 6.5, and (B) a 5:1 poly[Ru(vbpy)$_3^{2+}$/vba] film-modified GCE with 20-mer poly[dG] immobilized at pH 9.0 (50 mV/s scan rate, Ag/AgCl reference, 50 mM, pH 7.0 phosphate buffered solution).

Films treated with DNA probes at both pH values were then oxidized and compared to currents produced by film oxidation alone. In FIG. 6 it is clear that only those films treated with DNA probe at pH 6.5 produced currents with detectable catalytic enhancements. It was only these films in which DNA probe was reacted at pH 6.5 that showed catalytic current enhancement (8–13 $\mu$A of enhancement was typically observed).

Example 8

Quantification of immobilized probe. Based on electrochemical data, catalytic enhancements in oxidation current produced by poly[Ru(vbpy)$_3$$^{2+}$/vba] films in the presence of the 20-mer G probe indicate that approximately 10 $\mu$C more charge or $10^{-10}$ more moles of electrons (determined by voltammogram integration values) are transferred when compared to the oxidation of polymer alone. Radiolabeled probe was also used as a method to quantify the amount of DNA probe chemisorbed to a GCE surface at pH 6.5 and 9.0. Scintillation counts for surfaces treated with probe at pH 6.5 and 9.0 suggest that $7.4\times10^{-12}$ and $3.0\times10^{-14}$ moles had been immobilized respectively. These data are supported by separate labeling experiments that were done using a phosphorimaging screen for detection. Values obtained for the immobilized DNA probe were $8.0\times10^{-12}$ and $8.0\times10^{-13}$ mol at pH 6.5 and 9.0 using this alternate and more sensitive technique. Based on electrochemical measurements, $10^{-10}$ moles of guanine would need to be oxidized to observe a catalytic enhancement of 10 $\mu$C. Matched with the radiolabeling data, this would correspond to oxidation of near 50% of the guanine bases immobilized on the surface.

Example 9

Detection of hybridized nucleic acid. An electropolymerized film is prepared as in the previous examples via polymerization of Ru(bpy)$_3$$^{2+}$ and vba. An oligonucleotide probe containing an alternate base in place of guanine is attached to the film via a carbodiimide reaction. The electrode is then placed in contact with a solution that contains a target nucleic acid that contains guanine and is complementary to the immobilized probe. After hybridization occurs, the electrode is analyzed by cyclic voltammetry by scanning at 50 mV/s from 0. To 1.4 V. The electrochemical current is considered larger than for an electrode that has not been hybridized to the complementary, guanine-containing sequence.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. An electrode useful for the electrochemical detection of a nucleic acid, comprising:
   (a) a thin film that contains a metal complex, wherein said metal complex is an electropolymerization initiator, and wherein said metal complex is a mediator for the oxidation of a preselected base in the nucleic acid; and
   (b) functionalized moiety as part of said film to which the nucleic acid can be attached.

2. The electrode of claim 1, wherein the metal complex is selected from the group consisting of poly[Ru(vbpy)$_3$$^{2+}$] and poly[Ru(vbpy)$_3$$^{2+}$/vba], wherein vbpy is 4-vinyl-4'methyl-2,2'-bipyridine and vba is p-vinylbenzoic acid.

3. An electrode useful for the electrochemical detection of a preselected base in a nucleic acid, said electrode comprising:
   (a) a substrate having a conductive working surface; and
   (b) an electropolymerized film on said conductive working surface, said electropolymerized film comprising a co-polymer of a (i) a mediator for the oxidation of a preselected base in a nucleic acid: and (ii) a functionalized moiety having a carboxylate group to which the nucleic acid can be attached.

4. The electrode of claim 3, wherein the mediator is Ru(vbpy)$_3$$^{2+}$ and the functionalized moiety is p-vinylbenzoic acid.

* * * * *